United States Patent [19]

Nelson

[11] Patent Number: 4,727,863

[45] Date of Patent: Mar. 1, 1988

[54] REINFORCED ANKLE BRACE

[76] Inventor: Ronald E. Nelson, 405 Sunset La., Cambridge, Minn. 55008

[21] Appl. No.: 868,937

[22] Filed: May 30, 1986

[51] Int. Cl.⁴ .......................... A61F 3/00; A61F 13/00
[52] U.S. Cl. .................................... 128/80H; 128/166
[58] Field of Search ................. 128/80H, 80 D, 80 R, 128/165, 166, 166.5; 36/119, 89, 90, 91

[56] References Cited

U.S. PATENT DOCUMENTS

| | | |
|---|---|---|
| 325,280 | 9/1885 | Smadbeck et al. . |
| 332,727 | 12/1885 | McEwen . |
| 363,516 | 5/1887 | Hackey . |
| 605,299 | 6/1898 | Perrottet . |
| 765,024 | 7/1904 | Lueck ..................................... 36/90 |
| 832,613 | 10/1906 | Krieger . |
| 851,950 | 4/1907 | LeMat . |
| 921,563 | 5/1909 | Quenzer . |
| 929,179 | 7/1909 | Wood . |
| 1,037,441 | 9/1912 | Collis . |
| 1,081,366 | 12/1913 | Collis . |
| 1,084,197 | 1/1914 | Collis . |
| 1,231,332 | 6/1917 | Collis . |
| 1,717,609 | 6/1929 | Ludwig ............................... 128/166 |
| 2,096,677 | 10/1937 | Fassett .................................... 36/89 |
| 2,994,322 | 8/1961 | Cullen et al. . |
| 3,073,305 | 1/1963 | Biggs, Jr. et al. . |
| 3,298,365 | 1/1967 | Lewis . |
| 3,323,232 | 6/1967 | Danowsky .............................. 36/91 |
| 3,327,410 | 6/1967 | Park, Sr. et al. .................... 36/91 X |
| 3,970,083 | 7/1976 | Carrigan .............................. 128/166 |
| 4,187,844 | 2/1980 | Caprio, Jr. .......................... 128/166 |
| 4,237,874 | 12/1980 | Nelson . |
| 4,527,556 | 7/1985 | Nelson . |

FOREIGN PATENT DOCUMENTS 9531 of 1886 United Kingdom .................... 36/89

Primary Examiner—Clifford D. Crowder
Attorney, Agent, or Firm—Burd, Bartz & Gutenkauf

[57] ABSTRACT

An ankle support brace to provide generalized support to the ankle and specifically protect the anterior talofibular ligament from injury or aggravation of preexistent injury. A base is conformable to the foot and ankle region of the wearer and carries lateral and medial resilient stays. The stays are vertical in the upper part of the base and curve rearwardly in the lower part of the base around the medial malleolus and lateral malleolus. An anterior talofibular ligament support strap is fixed at one end to a lower part of the base positioned to be beneath the sole of the foot proximate the heel and extends distally around the foot. The other end of the support strap is fixed to a portion of the base positioned on the superior portion of the foot such that the support strap binds together the lower portion of the foot and the ankle bone to limit the permissible amount of stretching of the anterior talofibular ligament in a direction that would tend to injure it.

19 Claims, 7 Drawing Figures

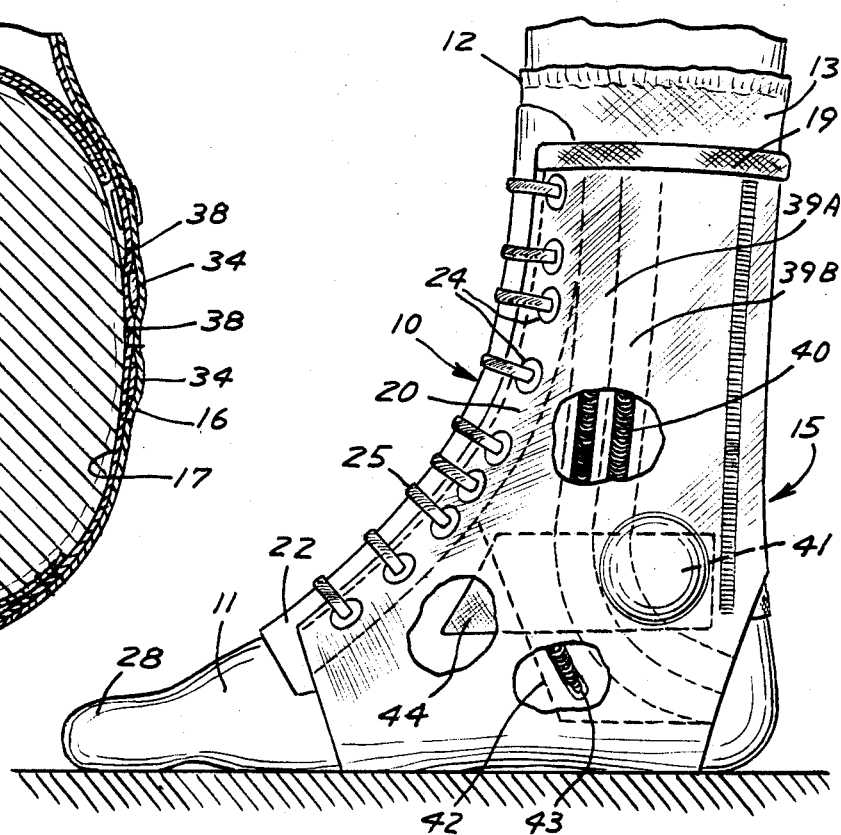
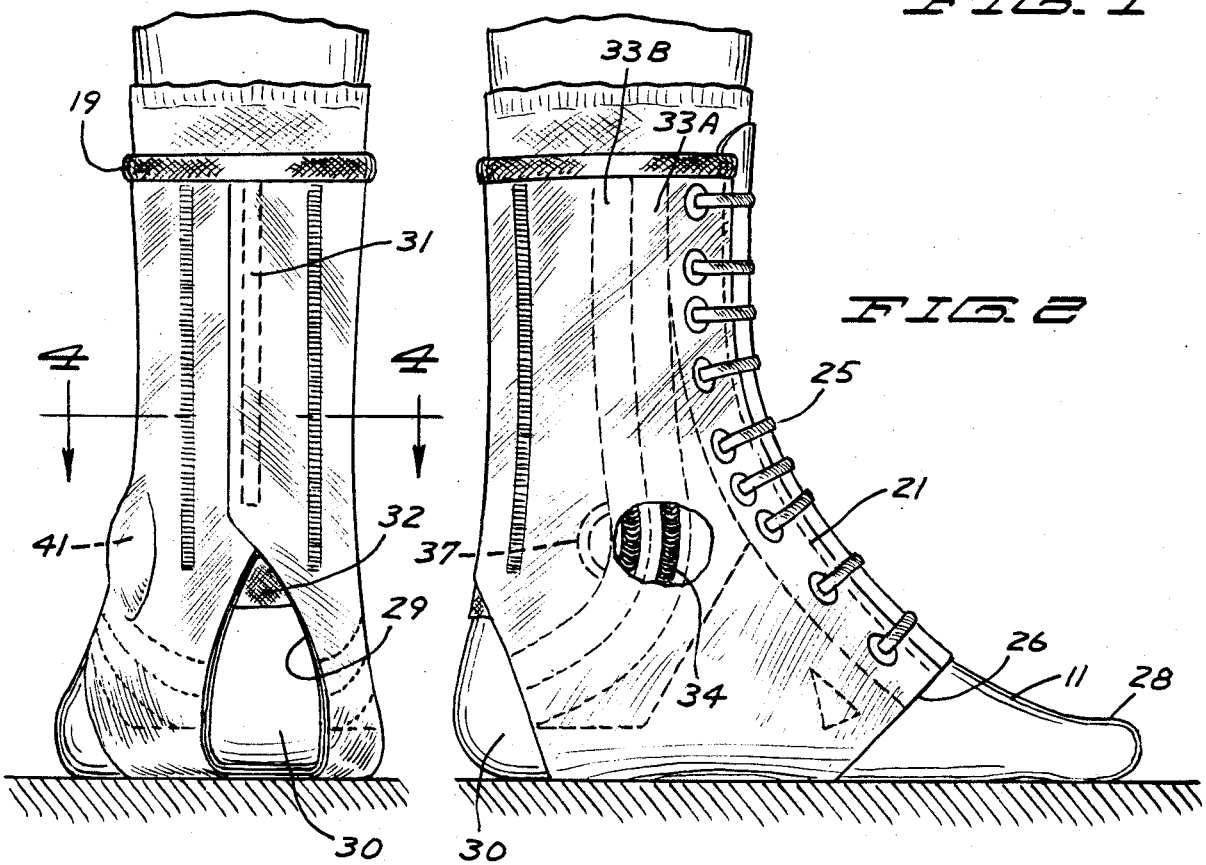

REINFORCED ANKLE BRACE

BACKGROUND OF THE INVENTION

The ankle joint is very stable and resistant to injury. However, since it is one of the most used and abused joints, it is nonetheless frequently injured, particularly upon participation in certain rugged sports, such as basketball and football. The ankle joint is the complex articulation joint of the fibula and tibia with the ankle bone or talus and the tarsal bones. The outer ankle knob or lateral malleolus is at the lower end of the fibula. The inner ankle knob or medial malleolus is at the lower end of the tibia. These are held tightly together by the tibiofibular ligaments to form the top half of the ankle joint or the receptacle known as a mortice which is occupied by the talus. The talus is held in the mortice by more ligaments. The inside ligament system comprises the deltoid ligament. The outside ligament system is more complex. The front ligament that goes forward from the lateral malleolus is called the anterior talofibular ligament. This ligament runs from the lateral malleolus to the ankle bone. A second ligament goes from the tip of the lateral malleolus straight down to the heel bone. This is called the calcaneofibular ligament. A third ligament, the posterior taleofibular ligament, runs directly back from the lateral malleolus to the ankle bone.

The most common injury in sports is an ankle sprain. This results when the ankle bone is forced or pried out of the mortice or ankle joint. It generally happens when the ankle is forceably rotated inward. A mild sprain occurs upon momentary displacement of the ankle bone and causes only mild stretching of the ligaments on the distal ankle. Severe strains involve tearing of ligaments upon dislocation of the ankle bone. When the ankle is forceably tipped inward, the first ligament to restrain this motion and, accordingly, the first to be injured is the anterior talofibular ligament. The next ligament to be injured, the calcaneofibular ligament, is seldom injured above, as usually the anterior talofibular ligament is injured first. Accordingly, it is important in the prevention of a sprain injury, or in preventing the aggravation of preexistent sprain injury, to protect first the anterior talofibular ligament and provide secondary protection for the calcaneofibular ligament. Various forms of gear are available to generally support and protect the ankle and deter it from movement in unintended direction. These include tape, elastic wrap and ankle braces of various types. However, such devices do not provide specific support to guard against injury to the anterior talofibular ligament and the calcaneofibular ligament.

SUMMARY OF THE INVENTION

The invention pertains to an ankle brace particularly adapted to specifically support the anterior talofibular ligament and the calcaneofibular ligament while providing generalized support to the ankle.

The brace includes a base that is to be wrapped around the foot in close conformance to the foot and ankle and secured by lacing at closable forward edges. The medial side of the base has elongate pockets which accommodate resilient stays or ribs. The upper portions of the pockets are vertical and the lower portions are rearwardly curved to curve around the medial malleolus. The lateral side of the brace also has elongate pockets which carry resilient stays or ribs. The upper portion of two of the pockets is vertical. The lower portions of two of the pockets plus a third pocket are rearwardly curved and extend across that portion of the foot in substantially normal or perpendicular relationship to the anterior talofibular ligament. These stays tend to exert an inward pressure on the anterior talofibular ligament in order to keep it in place. A cushion is fixed to the inside of the base on the lateral side and extends in parallel covering relationship to the anterior talofibular ligament. This cushion is disposed between the resilient stays and the surface of the foot and serves to disperse the pressure of the resilient stays and the base over the talofibular ligament. A support strap is fixed to the inside surface of the lateral side of the base. One end of the strap is fixed to the base proximate the location of the heel bone when the brace is fitted on a foot. The other end of the strap is fixed proximate the closable lateral edge of the base. The strap extends crosswise over the vicinity of the talofibular ligament when the base is fastened to the foot. The strap tends to compress the region between the heel bone and the superior surface of the lateral malleolus to prevent tension force being applied to the anterior talofibular ligament, as well as the calcaneofibular ligament.

IN THE DRAWINGS

FIG. 1 is a side elevational view of the lateral side of a foot wearing an ankle brace according to the present invention;

FIG. 2 is a side elevational view of the medial side of the foot and ankle brace of FIG. 1;

FIG. 3 is a rear elevational view of the foot and ankle brace of FIG. 1;

FIG. 4 is an enlarged sectional view of the ankle brace of FIG. 3 taken along the line 4—4 thereof;

DESCRIPTION OF A PREFERRED EMBODIMENT

Figure 5:
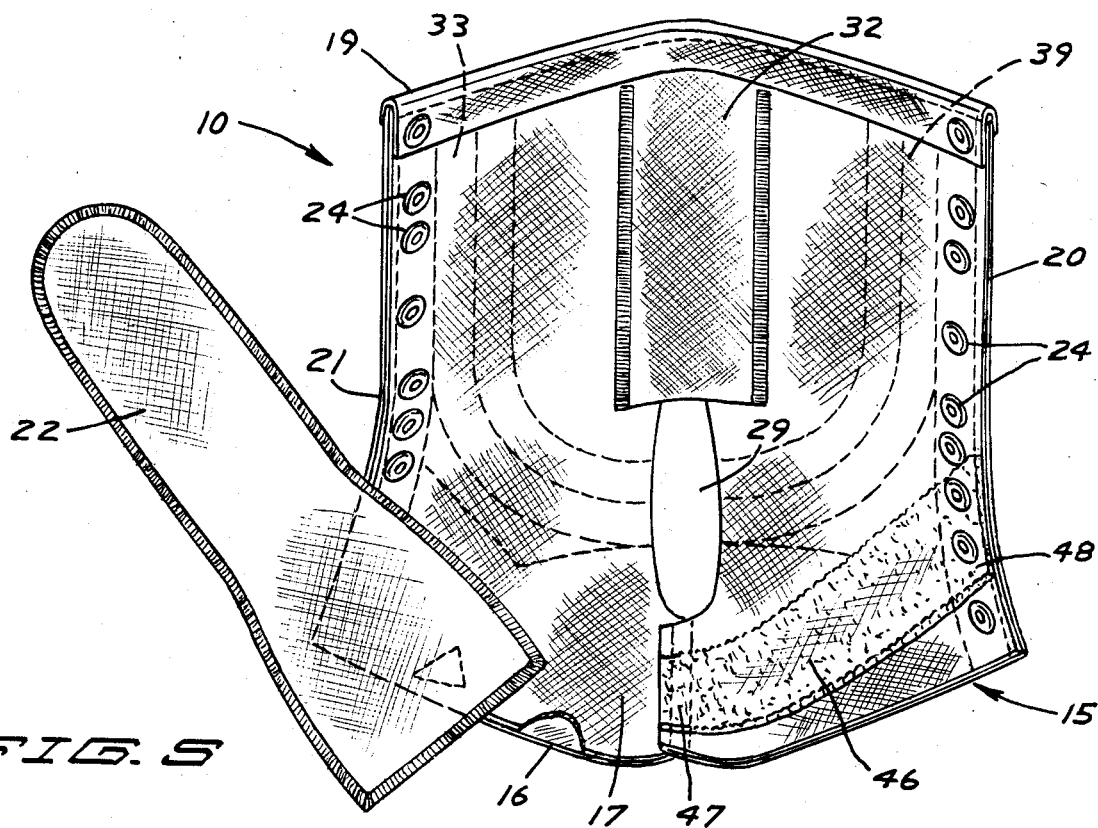
FIG. 5 is a front elevational view of the ankle brace of FIG. 1 in an open configuration for purposes of illustration showing the inside thereof.

Referring to the drawings, there is shown in FIGS. 1 through 3 an ankle brace indicated generally at 10 installed on the left foot 11 and an ankle region 12 of a person over a sock 13. Ankle brace 10 can be fitted on a bare foot or over a sock. The ankle brace 10 projects the ankle joint generally and specifically provides support and protection to the anterior talofibular ligament of the foot.

Ankle brace 10 includes a base 15 of flexible sheet material shaped to closely encompass the mid-foot portion and ankle of the wearer. As shown in FIG. 5, base 15 includes an outer layer 16 and a coextensive liner 17, which combine for strength and comfort. The outer layer 16 is a durable inelastic material, such as vinyl. The liner 17 is a soft material, such as brushed canvas, with the brushed or soft side facing the foot. Together the outer layer 16 and the liner 17 give strength and durability to the brace 10.

Figures 6, 7:
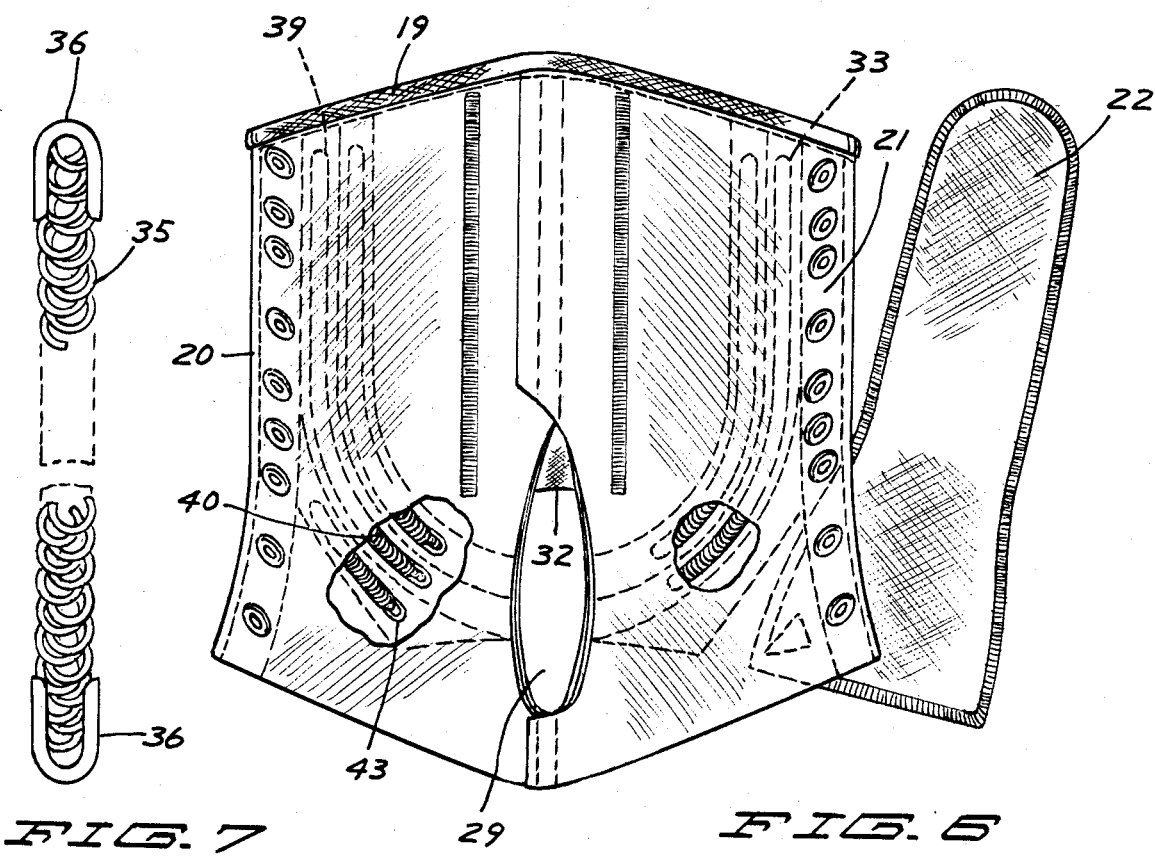
FIG. 6 is a rear elevational view of the ankle brace as shown in FIG. 5.
FIG. 7 is a fragmented front plan view of a retaining member or stay as used in the ankle brace of the invention.

Basee 15 has an upper edge 19 that encircles the leg while forward closable distal or lateral and proximal or medial edges 20, 21 move toward one another over a tongue 22 to close about the upper superior portion of the foot. A plurality of eyelets 24 are provided in the closable forward edges 20, 21. The eyelets 24 are grouped or spaced more closely together toward the center so that the brace can be more firmly tightened across the top of the foot. Eyelets 24 carry a shoelace 25 to be laced up and tied in the normal fashion. Lower forward edge 26 of the base 15 encircles the foot to provide an opening for the toes 28. The rear edges of the outer layer 16 and liner 17 come together along the rear of the leg at seam 31 in parallel relationship to the Achilles tendon. They are cut so as to provide a heel opening 29 with an upper curved portion to closely accommodate the anterior curve of the rear foot. When the base is worn on a foot, the heel 30 extends outwardly of the heel opening 29. As shown in FIGS. 5 and 6, an elastic strip 32 extends from the upper edge 19 down to and partially covering the heel opening 29. Elastic strip 32 is positioned to be in covering relationship to the Achilles tendon on the back of the foot. Elastic strip 32 tends to protect the Achilles tendon region of the foot.

A pair of elongate pockets 33A, 33B are formed on the medial side of the base forward of the medial malleolus indicated at 37 and carry resilient stiffening members or stays 34. As shown in FIG. 7, each stay 34 can be comprised of two helical spring elements interleaved and flattened having an elongated coiled body portion 35 with end caps 36. The pockets 33 are generally vertical or upright near the top of base 15 and curve rearwardly toward the bottom of base 15 in encircling relationship to the medial malleolus. The pockets 33 are formed by stitching 38 between the outer layer 16 and liner 17 of base 15. The stays 34 partially encircle the medial malleolus and lend support to the region of the medial malleolus and ankle.

The lateral side of base 15 and foot 11 are shown in FIG. 1. A second plurality of pockets formed along the side of the base 15 includes first and second pockets 39A, 39B carrying resilient stay memebers 40 located forward of the latereal malleolus indicated at 41. The pockets 39A, 39B are vertical in the upper portion of base 15 and curve rearwardly at the lower part of the base. The lower portion of the pockets 39 curve in a location encircling the forward portion of the lateral malleolus so as to intersect the anterior talofibular ligament at that region and provide inward pressure on the ligament. The pockets 39 are formed between the outer layer 16 and liner 17 in base 15. A third pocket 42 is curved and located forward of the curved portions of the pockets 39A, 39B and carries a foreshortened curved stay member 43, which is also disposed in intersecting relationship with respect to the anterior talofibular ligament. A cushion 44 formed of a soft material, such as foam or the like, is positioned between the outer layer 16 and liner 17 of base 15. Cushion 44 is located immediately ahead of and slightly beneath the lateral malleolus to partially fill a small void that exists in that region of the foot and provide support to it.

As shown in FIG. 5, an anterior talofibular ligament support strap 46 is sewn to the inside of base 15 in a position to bind the bottom of the foot proximate the heel to the top portion of the foot near the lateral malleolus and relieve strain that might otherwise be placed on the anterior talofibular ligament. Support strap 46 is formed of a relatively inelastic material approximately 2 inches (5 centimeters) in width. One end 47 of strap 46 is fixed to base 15 at the bottom thereof forward of the heel opening 29 so as to be in the approximate mid-foot area when installed on a foot. The strap 46 extends distally over the side of the foot. The other end 48 of strap 46 is fixed to the inside of base 15 near or at the lateral leading edge 20 in the vicinity of the lower to middle eyelets. Upon installation of base 15 on a foot, the second end 48 of strap 46 is located on the foot 11 somewhat opposite to the first end 47 with respect to the anterior talofibular ligament. Support strap 46 inhibits separation of the lower foot portion from the ankle portion in the direction that would otherwise tend to pull or sprain the anterior talofibular ligament.

In use, left and right ankle braces are provided for left and right feet. The base 15 is installed on the foot with the heel 30 protruding through the heel opening 29. Normally, thiswould be accomplished by inserting the foot through the top opening defined by upper edge 19 with the lace 25 already loosely in place. The foot is fitted in the base 15 with the tongue 22 positioned over the superior foot portion. The lace 25 is then tightened and tied at the top with the usual bow knot. The base can be installed over a bare foot or a sock. The foot is then placed in the usual athletic shoe. The medial and lateral stay members 33, 39 provide generalized support for the ankle in the upper region. The rearwardly curved lower portions of the stays provide support in the vicinity of the malleolus. In particular, the lateral stays 40 curve around the lateral malleolus in substantially intersecting relationship to the anterior talofibular ligament and provide some pressure against it. The cushion 44 somewhat follows and covers the same ligament. Support strap 46 binds the lower and upper foot portions together and limits the amount of separation permitted between them so as to inhibit or limit the amount of stretching of the anterior talofibular ligament. The elastic strip 32 in the back of base 15 covers and protects the Achilles tendon.

The embodiments of the invention in which an exclusive property or privilege is claimed are defined as follows:

1. An ankle brace to be worn on a foot and ankle in encompassing relationship to the lateral malleolus and medial malleolus of the ankle on the lateral and medial sides of the foots respectively, comprising:

a base of flexible sheet material shaped to encompass an ankle and at least the middle portion of a foot, having lateral and medial forward edges that come toward one another over the superior portion of the foot, and a portion that extends beneath the sole of the foot;

means cooperating with the forward edges of the base for tightly securing the base relative to a foot;

a support strap for protection of the anterior talofibular ligament of the foot, said strap having a first end secured to the inside of the base at a location generally beneath the sole of the foot, and a second end fixed to the inside of the base at a location proximate the lateral edge of the base to locate the support strap over the lateral side of the foot, the section of support strap between the first and second ends being unconnected to the base and of a length to bind together the upper and lower portions of the foot and ankle on opposite sides of the anterior talofibular ligament upon closure of the forward edges of the base over the superior portion of the foot.

2. An ankle brace to be worn on a foot and ankle in encompassing relationship to the lateral malleolus and medial malleolus of the ankle or the lateral and medial sides of foot respectively, comprising:

a base of flexible sheet material shaped to encompass an ankle and at least the middle portion of a foot, having lateral and medial forward edges that come toward one another over the superior portion of the foot, and a portion that extends beneath the sole of the foot;

means cooperating with the forward edges of the base for tightly securing the base relative to a foot;

a support strap for protection of the anterior talofibular ligament of the foot, said strap having a first end secured to the inside of the base at a location generally beneath the sole of the foot, and a second end fixed to the inside of the base at a location proximate the lateral forward edge of the base, to locate the support strap extending over the lateral side of the foot and tend to bind together the upper and lower portions of the foot and ankle on opposite sides of the anterior talofibular ligament;

a plurality of elongate lateral pockets on the lateral side of the base and located forward of and curving rearwardly under the lateral malleolus when the base is worn on a foot; and a corresponding plurality of resilient stay members located in the pockets.

3. The ankle brace of claim 2 including: a cushion fixed to the base at a location immediately forward of and slightly beneath the lateral malleolus.

4. The ankle brace of claim 2 wherein: said lateral pockets comprise three pockets, at least one of said pockets extending vertically upward from the location forward of the medial malleolus.

5. The ankle brace of claim 2 wherein: said lateral pockets comprise three pockets, at least two of said pockets extending vertically upward on the base from the location forward of the lateral malleolus.

6. The ankle brace of claim 5 including: a cushion fixed to the base at a location immediately forward of and slightly beneath the lateral malleolus.

7. The ankle brace of claim 6 wherein: said means to tightly secure the base relative to the foot includes a plurality of spaced apart eyelets located along the medial and lateral forward edges of the base, and a shoelace trained through the eyelets.

8. The ankle brace of claim 2 including: at least one medial pocket located on the medial side of the base and located forward of and curving rearwardly under the medial malleolus; and a resilient stiffening member located in the medial pocket.

9. The ankle brace of claim 8 including: two medial pockets, each extending vertically upward on the base from the location forward of the medial malleolus.

10. The ankle brace of claim 9 including: a cushion fixed to the base at a location immediately forward of and slightly beneath the lateral malleolus.

11. The ankle brace of claim 9 wherein: said lateral pockets comprise three pockets, at least one of said pockets extending vertically upward from the location forward of the lateral malleolus.

12. The ankle brace of claim 8 including: a heel opening in said base for accommodation of the heel, an elastic strip fixed to the inside of the base and having a portion located in partially covering relationship to the heel opening.

13. An ankle brace to be worn on a foot for support of the anterior talofibular ligament and encompassing relationship to the lateral malleolus and medial malleolus, comprising:

base means shaped for conformance to the ankle and middle foot portion of a wearer;

means for securely installing the base on a foot;

an anterior talofibular ligament support strap fixed to the inside of the base;

said strap having a first end secured to the base at a position beneath the sole of the foot, said strap extended upwardly around the lateral side of the foot and having a second end fixed to the base at a superior location on the foot, sai strap being unconnected to the base between the first and second ends, said strap of a length to inhibit an amount of relative movement between the foot and lateral malleolus sufficient to strain the anterior talofibular ligament when the base is installed on a foot.

14. An ankle brace to be worn on a foot for support of the anterior talofibular ligament and in encompassing relationship to the lateral malleolus and medial malleolus, comprising:

base means shaped for conformance to the ankle and middle foot portion of a wearer;

an anterior talofibular ligament support strap fixed to the inside of the base;

said strap having a first end secured to the base at a position beneath the foot, said strap extended upwardly around the lateral side of the foot and having a second end fixed to the base at a superior location on the foot, said strap of a length to inhibit an amount of relative movement between the foot and lateral malleolus sufficient to strain the anterior talofibular ligament;

resilient stay means on the lateral side of the base means extending from a position forward of the lateral malleolus and curving rearwardly and beneath the lateral malleolus.

15. The ankle brace of claim 14 including: resilient stay means located on themedial side ofthe base means extending from a position forwrad of the medial malleolus and curving rearwardly and beneath the medial malleolus.

16. The ankle brace of claim 15 wherein: said base means includes first and second sheet members, the first sheet member being an outer layer, and the second sheet member being a liner.

17. The ankle brace of claim 16 including: a cushion fixed to the base means at a location immediately forward of and slightly beneath the lateral malleolus.

18. An ankle brace to be worn on a foot and ankle in encompassing relationship to the lateral malleolus and medial malleolus of the ankle on the lateral and medial sides of the foot respectively, comprising:

a base of flexible sheet material shaped to encompass an ankle and at least the middle portion of a foot, having lateral and medial forward edges that come toward one another over the superior portion of the foot, and a portion that extends beneath the sole of the foot;

means coperating with the forward edges of the base for tightly securing the base relative to a foot;

a plurality of elongate lateral pockets locate on the lateral side of the base and located forward of and curving rearwardly under the lateral malleolus when the base is worn on a foot; and a corresponding plurality of resilient stay members located in the lateral pockets; and at least one medial pocket located on the medial side o the base and located forward of and curving rearwardly under the medial malleolus; and a resilient stay member located in the medial pocket.

19. The ankle brace of claim 18 wherein: said means to tightly secure the base relative to the foot includes a plurality of spaced apart eyelets located along the medial and lateral forwared edges of the base, and a shoelace trained through the eyelets.

* * * * *

UNITED STATES PATENT AND TRADEMARK OFFICE
CERTIFICATE OF CORRECTION

PATENT NO. : 4,727,863

DATED : March 1, 1988

INVENTOR(S) : Ronald E. Nelson

It is certified that error appears in the above-identified patent and that said Letters Patent is hereby corrected as shown below:

| | |
|---|---|
| Col 2, l. 51 | "projects" should be --protects-- |
| Col 2, l. 65 | "Basee" should be --Base-- |
| Col 4, l. 15 | "thiswould" should be --this would-- |
| Col 5, l. 1 | "or" should be --on-- |
| Col 6, l. 7 | "sai" should be --said-- |
| Col 6, l. 32 | "themedial" should be --the medial-- |
| Col 6, l. 32 | "ofthe" should be --of the -- |
| Col 6, l. 33 | "forwrad" should be --forward-- |
| Col 6, l. 52 | "coperating" should be --cooperating-- |
| Col 6, l. 54 | "locate" should be --located-- |
| Col 6, l. 61 | "o" should be --of-- |

Signed and Sealed this

Twenty-fifth Day of December, 1990

Attest:

HARRY F. MANBECK, JR.

*Attesting Officer*      *Commissioner of Patents and Trademarks*